United States Patent

Hanwong

[11] Patent Number: 5,171,240
[45] Date of Patent: Dec. 15, 1992

[54] INSTRUMENT FOR IMPLANTATION OF A PROSTHESIS IN A STAPEDECTOMY PROCEDURE

[76] Inventor: Yuthaphong Hanwong, Department of ENT, Chulalongkorn Hospital, Bangkok, Thailand

[21] Appl. No.: 541,960

[22] Filed: Jun. 22, 1990

[51] Int. Cl.⁵ .............................................. A61B 17/00
[52] U.S. Cl. ........................................ 606/1; 606/99; 606/109
[58] Field of Search ................. 606/91, 99, 100, 107, 606/109, 108, 138, 1

[56] References Cited

U.S. PATENT DOCUMENTS

| | | | |
|---|---|---|---|
| 829,409 | 8/1906 | Manning | 606/108 X |
| 3,077,879 | 2/1963 | Knoch . | |
| 4,222,382 | 9/1980 | Antonsson et al. | 606/100 |
| 4,365,957 | 12/1982 | Das . | |
| 4,580,560 | 4/1986 | Straith | 606/108 |
| 4,619,256 | 10/1986 | Horn | 606/107 |
| 4,642,121 | 2/1987 | Keller | 606/99 X |
| 4,927,425 | 5/1990 | Lozier | 606/99 |
| 4,991,567 | 2/1991 | McCuen et al. | 606/107 X |

OTHER PUBLICATIONS

Catalog, Micro-Surgery Instruments and Implants, Richards Manufacturing Co., 1965.

Primary Examiner—Michael H. Thaler
Attorney, Agent, or Firm—Shlesinger, Arkwright & Garvey

[57] ABSTRACT

An instrument for holding a prosthesis in stapedectomy procedure comprises a handle, a shank attached to the handle, and a holder attached to a free end of the shank for holding the prosthesis. The holder includes a wedge-shaped opening for securing the prosthesis and a stop for limiting the rotation of the prosthesis in an axis transverse to the prosthesis in the wedge-shaped opening.

15 Claims, 3 Drawing Sheets

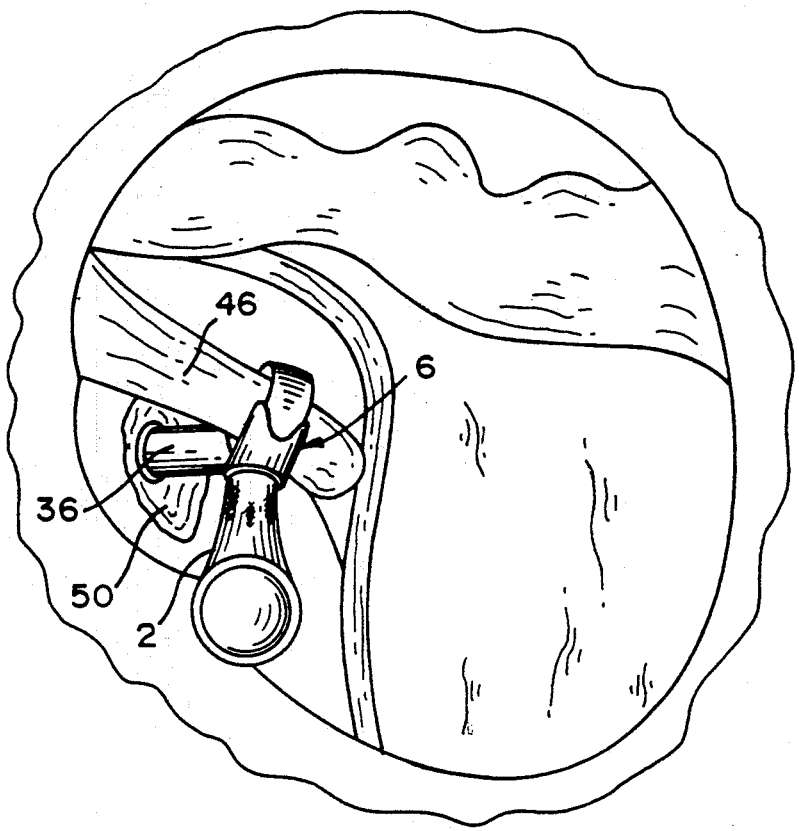
FIG_10
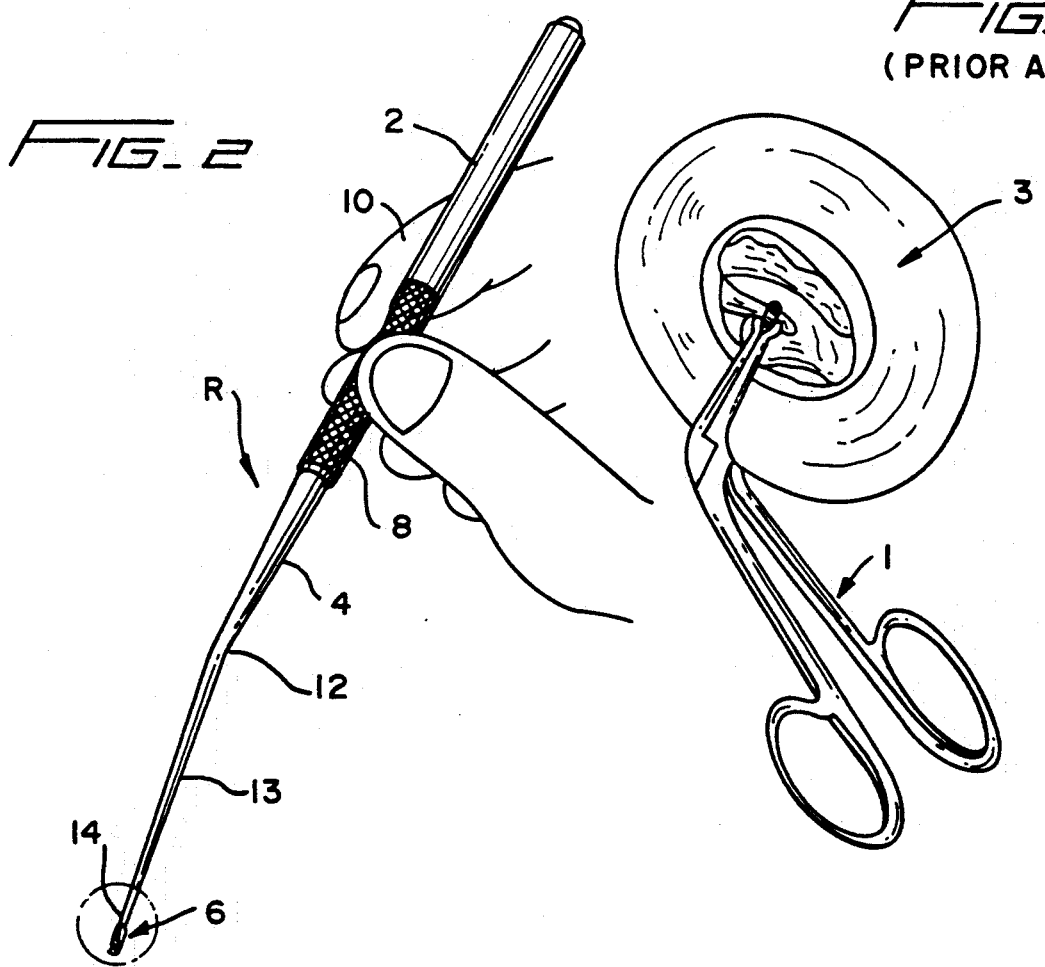
FIG_1 (PRIOR ART)
FIG_2

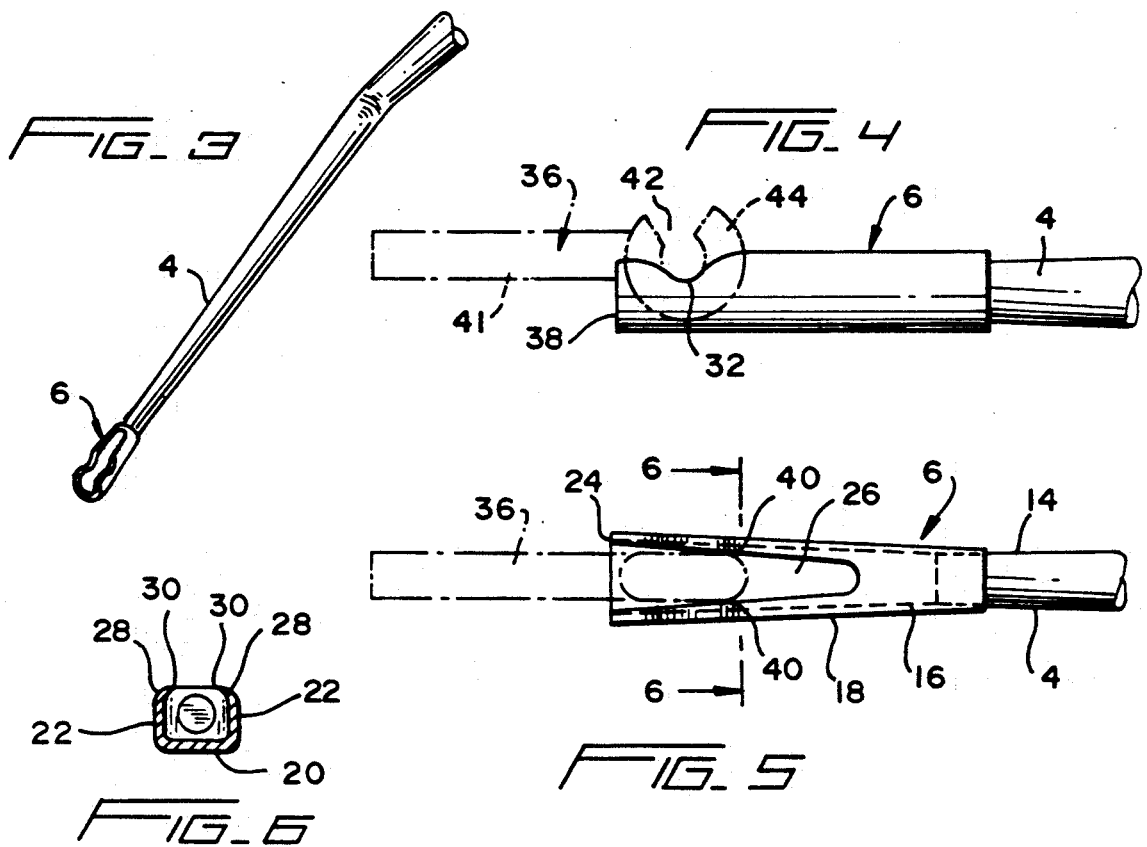
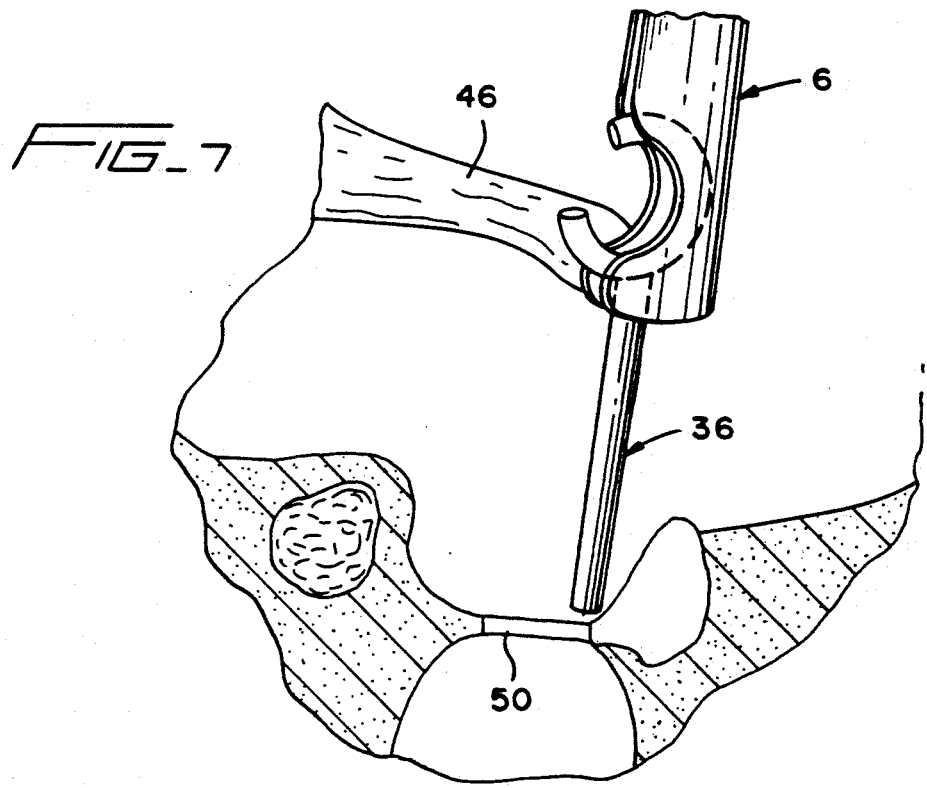

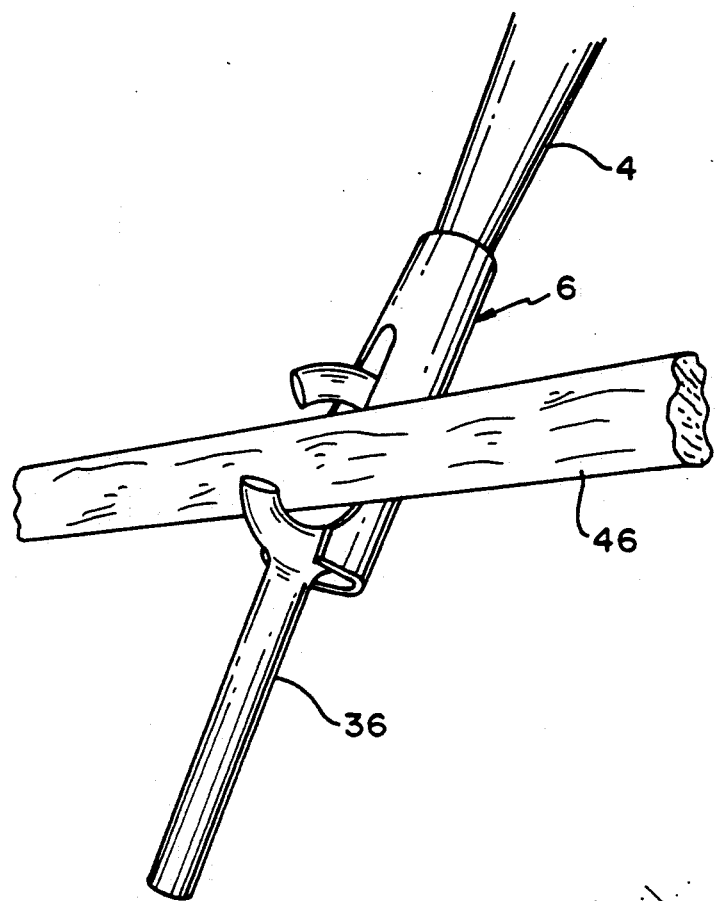
FIG_9
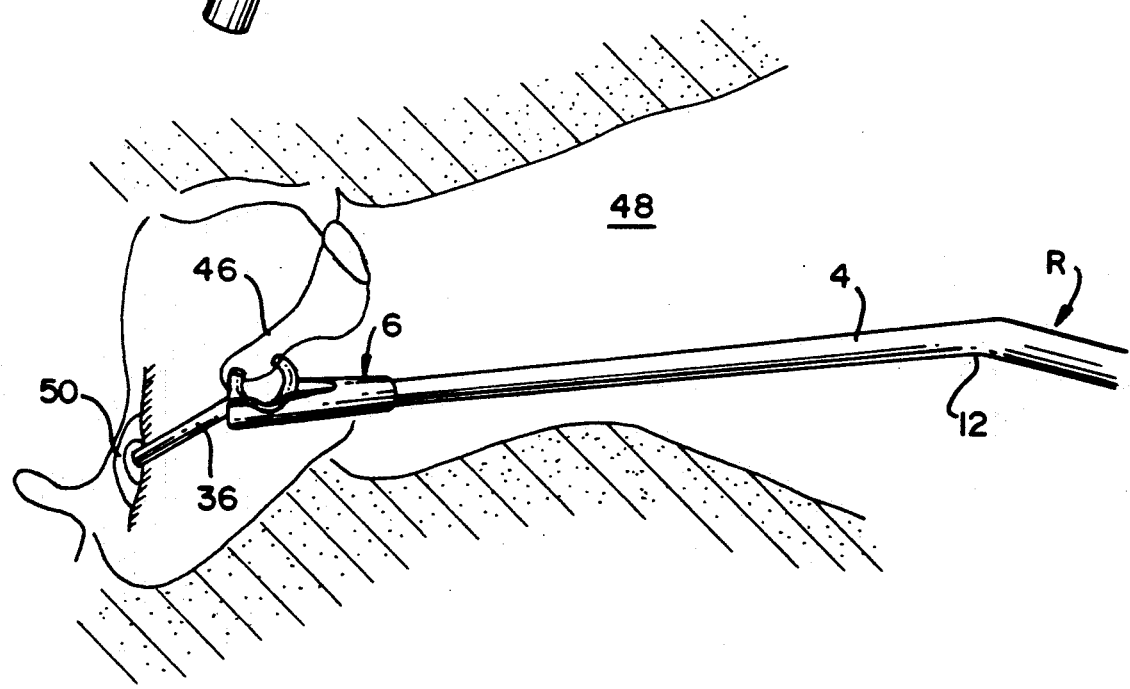
FIG_8

INSTRUMENT FOR IMPLANTATION OF A PROSTHESIS IN A STAPEDECTOMY PROCEDURE

FIELD OF THE INVENTION

The present invention relates generally to a medical instrument for use in implanting a prothesis in an ear, and in particular to an instrument for implanting a prosthetic piston in the middle ear in a stapedectomy procedure.

BACKGROUND OF THE INVENTION

The middle ear comprises the malleus (hammer), the incus (anvil), and the stapes (stirrup). They form a short bony chain spanning between the external ear and the middle ear. The malleus resembles a club, the incus a premolar tooth, and the stapes a stirrup.

The malleus and the incus have a tightly fitting joint between them. The long process of the incus is bent near its lower end and carries a small bony knob that forms a loose joint with the head of the stapes. The stapes is about 3 millimeters high and weighs slightly less than 3 milligrams. It lies almost horizontally at right angles to the long process of the incus. The footplate of the stapes fits neatly in the oval window, which is one of the two openings in the wall of the bony labyrinth, where it is held in place by the annular ligament.

When sound is transmitted through the ear canal, the malleus, which is attached to the ear drum, moves in and out with the movements of the drum membrane in response to the sound. The incus that is attached to the malleus, moves with the malleus. The stapes that is coupled to the incus does not move in and out of the oval window, but rocks about the lower pole of its footplate as it transmits the vibrations to the inner ear. The footplate of the stapes fits neatly into the oval window, thereby concentrating the sound in a small area.

A disease of the middle ear known as fixation of the stirrup by otosclerosis causes progressive hearing loss in early and middle adult life. Otosclerosis is the abnormal formation of spongy bone in the inner ear that causes the stapes to become immobilized. In its early and actively expanding stage the nodule of the softened bone becomes large enough to reach the oval window containing the footplate of the stirrup. Increasing pressure caused by expanding nodule begins to impede the vibratory movements of the stapes in response to sound striking the drum membrane.

Fixation of the stirrup bone can be corrected surgically by an operation known as stapedectomy. This operation involves the removal of the affixed stirrup bone and replacement by a plastic or wire substitute, such as a TEFLON (registered trademark) piston. The operation restores the vibration characteristics of the chain of tiny bones of the middle ear.

The operation is extremely delicate and difficult since the middle ear bones are the smallest bones of the body. The surgical implantation of a replacement stapes generally uses an instrument called cupforceps or alligator forceps 1 to hold the prosthetic piston, as best shown in FIG. 1. The cup forceps or alligator forceps 1 are held in similar fashion as holding a pair of scissors. This is inherently unstable, since the surgeon is applying closure pressure on the instrument while at the same time trying to position the prosthetic piston in place. This typically causes vibration at the tip of the instrument if the surgeon is inexperienced. Another factor contributing to the difficulty of the operation is that the operation is done through the ear canal with the use of an ear speculum 3 and a microscope, as best shown in FIG. 1. Because the tip of the cupforceps is typically thick in relation to the prosthetic piston, and because of the narrow field of the operation, it is difficult to see the prosthetic piston tip for accurate implantation into the top of the footplate and for attaching to the lenticular process of the incus. This difficulty is highlighted in FIG. 1, which is a view into the ear canal through the ear speculum 3.

There is therefore a need for a novel instrument that will resolve the above-mentioned difficulties.

OBJECTS AND SUMMARY OF THE INVENTION

It is therefore an object of the present invention to provide an instrument that simplifies the implantation of a prosthetic piston in a stapedectomy procedure.

It is another object of the present invention to provide an instrument that does not obstruct the narrow field of view of the surgeon when implanting a prosthetic piston in a stapedectomy procedure.

It is still another object of the present invention to provide an instrument that is relatively much easier to use than cupforceps or alligator forceps, which are typically used in a stapedectomy procedure.

It is yet another object of the present invention to provide an instrument that minimizes the vibration at the tip of the instrument during implantation in a stapedectomy procedure due to inexperience of the surgeon or inherent difficulty associated with using cupforceps or alligators forceps.

It is still further another object of the present invention to provide an instrument that enables even an inexperienced surgeon to accurately implant a prosthetic piston in a stapedectomy procedure.

It is an object of the present invention to provide an instrument without any moving parts, thereby simplifying its use and manufacture.

It is another object of the present invention to provide an instrument that is comfortable to handle thereby to minimize vibration at the tip of the instrument and provide relatively greater ease in implanting a prosthesis in a stapedectomy procedure.

In summary, the present invention provides an instrument for implantation of a prosthetic piston in a stapedectomy procedure that makes the procedure relatively easier to do.

BRIEF DESCRIPTION OF THE DRAWINGS

FIG. 1 is a view looking into the ear canal with an ear speculum during a stapedectomy procedure using prior art cupforceps.

FIG. 2 is a perspective view of an instrument according to the present invention in a normally held position.

FIG. 3 is an enlarged, fragmentary, perspective view of the instrument of FIG. 2, showing a prosthetic holder at the tip thereof.

FIG. 4 is an enlarged, fragmentary, side elevational view of the tip of the instrument of FIG. 2, showing a prosthetic piston in dashed lines secured thereby.

FIG. 5 is an enlarged, fragmentary, top elevational view of the tip of the instrument of FIG. 2, showing a prosthetic piston in dashed lines secured thereby.

FIG. 6 is a cross-sectional view taken along line 6—6 in FIG. 5.

FIG. 7 is an enlarged, fragmentary, perspective view of the middle ear, with portions shown in cross-section, and including an enlarged fragmentary perspective view of the tip of the instrument of FIG. 2 showing a prosthetic piston secured thereby.

FIG. 8 is an enlarged, longitudinal cross-sectional view through the ear canal, showing a fragmentary view of the instrument with a prosthetic piston secured thereto while being positioned into the middle ear.

FIG. 9 is a fragmentary, enlarged perspective view of the tip of the instrument of FIG. 2 with a prosthetic piston secured thereby, showing the prosthetic piston secured to the incus.

FIG. 10 is a view looking down into the ear canal, showing the prosthetic piston held by the tip of the instrument of FIG. 2 and secured to the incus and fitted into a hole in the footplate of a previously removed stapes in the oval window.

These and other objects of the present invention will become apparent from the following detailed description.

DETAILED DESCRIPTION OF THE INVENTION

An instrument R according to the present invention is disclosed in FIG. 2. The instrument R includes a handle 2, a shank 4 secured to or integral with the handle 2, and a holder 6 secured to a free end of the shank 4. The instrument R is preferably made from stainless steel or other materials suitable for use in the medical field. The handle 2 includes a roughened surface 8, such as provided by knurling or other conventional means, to provide a frictional gripping surface to a user. The center of gravity of the instrument R is preferably located in the handle 2 above the roughened surface 8, such that the instrument R when gripped will naturally rest on the index finger 10 of the user, as best shown in FIG. 2. This provides a comfortable and substantially vibration free grip on the instrument R.

The shank 4 is bent at 12 with an obtuse angle. A portion 13 below the bend 12 is long enough to permit its insertion into the ear canal and into the middle ear. The bend 12 thereby allows the hand of the surgeon to be offset to the side of the ear canal opening to permit the surgeon an unobstructed view into the ear canal when using the instrument R. The shank 4 preferably tapers downwardly from the handle 2 to the tip 14 where the holder 6 is secured. The handle 2 is preferably cylindrical for ease of manufacture, to provide a comfortable grip and to provide maneuverability during use of the instrument R. The shank 4 is preferably conical in shape to permit greater visibility at the tip 14.

The holder 6 includes a hollow member having a tubular portion 16 attached to the tip 14 of the shank 4 and an integral trough portion 18, as best shown in FIG. 5. The trough portion 18 includes a bottom wall 20 and two opposed side walls 22, as best shown in FIG. 6. The trough portion 18 includes an end opening 24 and a wedged-shaped top opening 26, as best shown in FIGS. 4, 5 and 6. The opening 26 is directed away from the direction of bend 12.

The sidewalls 22 each includes an upper edge 28 bent inwardly and substantially transverse thereto and tapers into a knife edge 30, as best shown in FIG. 6. A prosthetic piston 36, typically made of plastic such as TEFLON (registered trademark), is positioned in the trough portion 18 between the side walls 22 and is wedged between the knife edges 30 that form the wedge-shaped top opening 26. The side walls 22 prevent the prosthesis from rotating from side to side in the direction of the side walls. The bottom wall 20 at the end opening 24 provides a stop means 38 for limiting the rotation of the prosthetic piston 36 about wedge points 40 in an axis transverse to the prosthetic piston 36, as best shown in FIGS. 4 and 5. Each sidewall 22 includes a curved recess 32 that lines up with an annular opening 34 of the prosthetic piston 36 to facilitate installation of the prosthesis, as best shown in FIGS. 4 and 9.

The holder 6 is preferably made of stainless steel, but other suitable materials can be used. The sidewalls 22 are spaced apart from each other at a distance adapted to accept a portion of the prosthetic piston 36.

The holder 6 is preferably attached to the tip 14 of the shank 4 by welding or swedging.

OPERATION

The prosthetic piston 36 includes a piston portion 41 and an annular loop 44 disposed at one end of the prosthesis. The prosthetic piston 36 is secured to the holder 6 by positioning the annular loop 44 in the trough portion 18 of the holder 6 and pushing the annular loop 44 into the wedge-shaped opening 26. The knife edges 30 bite into the plastic annular loop 44 and help retain the prosthesis in the holder 6 while it is being positioned in the middle ear, as best shown in FIGS. 4 and 5.

The stapes in the middle ear are surgically removed in a conventional manner. The length of the prosthetic piston 36 is then measured by securing it to the instrument R and making a direct measurement at the footplate, thereby providing a more accurate measurement than the prior conventional method of using a measuring rod.

A small hole is then made on the remaining footplate of the previously removed stapes. The small hole is adapted to the size of the prosthetic piston 36. The footplate of the stapes also may be removed if desired by using the so-called large hole technique.

An opening 42 is cut at the annular loop 44 of the prosthetic piston 36, as best shown in FIG. 4. The opening 42 is adapted to enable the annular loop 44 to slip through the lenticular process of the incus 46, as best shown in FIG. 9. The instrument R is then inserted into the external ear canal 48 and into the middle ear until the prosthetic piston 46 is positioned into the small hole in the footplate in the oval window, generally designated at 50, as best shown in FIG. 8. The annular loop 44 is then pressed into the inwardly curving portion of the lenticular process of the incus 46. The prosthetic piston 36 is installed at the posterior of the lenticular process of the incus 46, as best shown in FIG. 8.

After the prosthetic piston 36 is securely in place in the small hole and in the lenticular process of the incus 46, the instrument R is retrieved by pulling it parallel to the ear canal about one millimeter beyond the prosthetic piston 36 to disengage the annular loop 44 from the wedge-shaped opening 26. The trough portion 18 is then disengaged away from the prosthetic piston 36. Finally, the instrument R is pulled out of the ear canal.

To remove the prosthetic piston 36 from the lenticular process of the incus 46, the holder 6 is secured to the prosthetic piston 36 at the annular loop 44 as described in the above. The instrument R is then slowly rotated to the left or right so that the prosthetic piston 36 is disengaged from the lenticular process of the incus 46 through the opening 42 in the annular loop 44. The prosthetic piston 36 is then removed from the ear canal.

With the use of the instrument R the surgeon has a complete view of the tip of the instrument R during the whole procedure, as best shown in FIG. 10.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

I claim:

1. An instrument for holding a prothesis in a medical procedure, comprising:
   a) a handle;
   b) a shank attached to said handle;
   c) a trough secured to a free end of said shank for holding a prothesis;
   d) said trough having an end opening, a wedge-shaped top opening, a bottom wall and opposed side walls;
   e) said top opening tapering inwardly from said end opening toward said shank for wedging a portion of the prothesis therein, thereby securing the prothesis for implantation and removal;
   f) said side walls including upper edges; and
   g) said upper edges are bent inwardly substantially transverse to said side walls to provide gripping means for the prothesis.

2. An instrument as in claim 1, wherein:
   a) said shank includes a bend; and
   b) said top opening is directed away from the direction of said bend.

3. An instrument as in claim 1, wherein:
   a) said upper edges taper into a knife edge.

4. An instrument as in claim 1, wherein:
   a) said side walls include oppositely disposed curved recesses.

5. An instrument as in claim 1, wherein:
   a) said handle is cylindrical.

6. An instrument as in claim 1, wherein:
   a) said handle includes a roughened surface for providing a frictional gripping surface for the user.

7. An instrument as in claim 1, wherein:
   a) said handle includes a greater weight of said instrument than said shank.

8. An instrument as in claim 1, wherein:
   a) said shank is bent with an obtuse angle.

9. An instrument as in claim 1, wherein:
   a) said shank tapers from said handle toward said trough.

10. An instrument for holding and positioning a prosthesis within an ear in a stapedectomy procedure, said instrument comprising:
    a) a longitudinal member;
    b) said member having a handle portion and a shank portion;
    c) a pair of oppositely disposed walls secured at a free end of said shank portion;
    g) said pair of walls including a pair of oppositely disposed edge portions bent inwardly toward each other defining a wedge-shaped opening from wide to narrow toward said shank portion for securing a portion of a prosthesis therebetween;
    e) a stop for limiting the rotation of the prosthesis in said pair of walls about an axis transverse to the prosthesis;
    f) said pair of walls including a tubular portion at one end thereof, said tubular portion being attached to said shank portion.

11. An instrument as in claim 10, wherein:
    a) said tubular portion is attached to said shank by welding.

12. An instrument as in claim 10, wherein:
    a) said tubular portion is attached to said shank by swedging.

13. An instrument as in claim 10, wherein:
    a) said edge portions taper into a knife edge.

14. An instrument as in claim 10, wherein:
    a) said pair of walls include includes oppositely disposed curved recesses.

15. An instrument as in claim 10, wherein:
    a) said shank includes a bend; and
    b) said wedge-shaped opening is directed away from the direction of said bend.

* * * * *